(12) United States Patent
Fornarelli

(10) Patent No.: US 10,512,738 B2
(45) Date of Patent: Dec. 24, 2019

(54) DUAL CHAMBER VAPORIZATION TANK

(71) Applicant: AVANZATO TECHNOLOGY CORP., Chicago, IL (US)

(72) Inventor: Thomas Fornarelli, Chicago, IL (US)

(73) Assignee: AVANZATO TECHNOLOGY CORPORATION, Chicago, IL (US)

( * ) Notice: Subject to any disclaimer, the term of this patent is extended or adjusted under 35 U.S.C. 154(b) by 0 days.

(21) Appl. No.: 16/182,574

(22) Filed: Nov. 6, 2018

(65) Prior Publication Data
US 2019/0134320 A1    May 9, 2019

Related U.S. Application Data

(60) Provisional application No. 62/582,293, filed on Nov. 6, 2017.

(51) Int. Cl.
*A24F 47/00* (2006.01)
*A61M 11/04* (2006.01)
*H05B 3/44* (2006.01)
*A24F 7/02* (2006.01)
*A61M 15/00* (2006.01)
*A61M 15/06* (2006.01)

(52) U.S. Cl.
CPC .............. *A61M 11/042* (2014.02); *A24F 7/02* (2013.01); *A24F 47/008* (2013.01); *A61M 15/002* (2014.02); *A61M 15/0021* (2014.02); *A61M 15/06* (2013.01); *H05B 3/44* (2013.01); *H05B 2203/021* (2013.01)

(58) Field of Classification Search
None
See application file for complete search history.

(56) References Cited

U.S. PATENT DOCUMENTS

| | | | |
|---|---|---|---|
| 2015/0150308 A1* | 6/2015 | Monsees | A24F 47/006 131/329 |
| 2017/0196265 A1* | 7/2017 | Liu | A24F 47/008 |
| 2017/0238611 A1* | 8/2017 | Buchberger | A61M 15/0091 |
| 2017/0258141 A1* | 9/2017 | Chen | H05B 3/04 |
| 2018/0184722 A1* | 7/2018 | Murison | F04B 43/046 |

* cited by examiner

*Primary Examiner* — Michael J Felton
(74) *Attorney, Agent, or Firm* — Flener IP & Business Law; Zareefa B. Flener; Ayhan E. Mertogul

(57) ABSTRACT

A dual chamber vaporization tank comprises an inner tube, an intermediate tube, an outer tube, and a mouthpiece assembly. An e-liquid chamber is defined by a first annulus between the inner tube and the intermediate tube. The tank further comprises a porous ceramic ring having a heating coil disposed on an inner surface and an outer surface in fluid communication with the e-liquid chamber. An airflow path is defined from the surrounding air through an airflow aperture into a second annulus between the intermediate tube and the outer tube, along the second annulus in a first direction, through the heating coil in a second direction opposite the first direction, and through the inner tube.

20 Claims, 5 Drawing Sheets

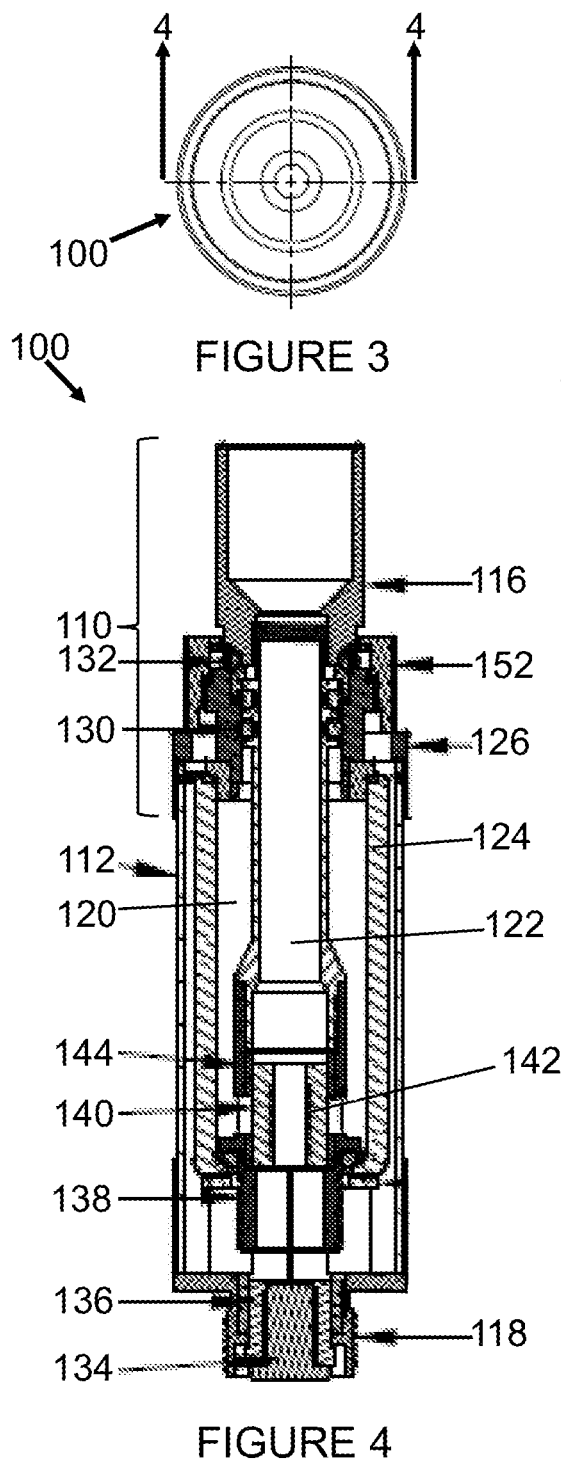

DUAL CHAMBER VAPORIZATION TANK

CROSS-REFERENCE TO RELATED APPLICATIONS

This application claims the benefit of priority to U.S. Provisional Patent Application No. 62/582,293 filed on Nov. 6, 2017 and incorporated in its entirety by reference herein.

FIELD OF THE INVENTION

The present invention relates to vaporization devices. More specifically, the present invention relates to a tank for a vaporization device with top flow air intake holes.

BACKGROUND

Personal vaporization devices that store substances to be vaporized include, for instance, inhalers for asthma treatment, and medicinal and recreational vaporization devices for personal use. Some personal vaporization devices have air intake holes at or near the bottom of a chamber or tank for containing the electronic liquid ("e-liquid"). Upon an inhalation of the user air is drawn into the device and flows over or past a heating coil that vaporizes the e-liquid into a vaporized product that travels through a mouthpiece of the device to be inhaled by the user. However, air holes disposed at the bottom of an e-liquid tank promotes leakage of the e-liquid out of the device through the holes. A solution to this problem is to locate air intake holes at a top side of the e-liquid tank, referred to as a top airflow tank.

The current state of the art for top airflow tanks brings air into a vapor tube assembly from a port by the mouth piece. The air travels away from the mouthpiece in an annular space between a center tube that feeds vapor to the mouthpiece and an annular tank. One such design is illustrated in U.S. Patent Application Publication No. 2018/0153220. However, problems exist with the current state of the art.

Ambient air traveling down around the center tube helps pull up vapor from the heating coil but does not pass through the heating coil. Therefore, the ambient air in existing designs pulls out only a fraction of the vapor from the region of the heating coil as compared to a design where the ambient air travels through the heating coil and pulls out substantially all the vapor therefrom.

Another problem of current top airflow tank designs is that the device and e-liquid start off at room temperature, but puff after puff raises the temperature of the device and the heating coil because there is insufficient airflow through the device and especially through the heating coil. Elevated internal temperatures can cause the e-liquid to thin and change properties. However, ambient air flowing through the coil has a beneficial cooling effect on the device by cooling the heating coil, which helps keep the e-liquid from thinning and over saturating the heating coil and changing the properties of the e-liquid, which ensures a consistent vapor production on every puff. Therefore, there is a need for a top airflow tank that includes airflow through the heating coil.

SUMMARY OF THE INVENTION

According to one aspect of the invention, a dual chamber vaporization tank comprises an inner tube, an intermediate tube, an outer tube, and a mouthpiece assembly. An e-liquid chamber is defined by a first annulus between the inner tube and the intermediate tube. The tank further comprises a porous ceramic ring having a heating coil disposed on an inner surface and an outer surface in fluid communication with the e-liquid chamber. An airflow path is defined from the surrounding air through an airflow aperture into a second annulus between the intermediate tube and the outer tube, along the second annulus in a first direction, through the heating coil in a second direction opposite the first direction, and through the inner tube.

According to another aspect of the invention, a dual chamber vaporization tank, comprises an e-liquid chamber defined by a first annulus between an inner tube and an intermediate tube. An airflow path is defined from the surrounding air through an airflow aperture into a second annulus between the intermediate tube and the outer tube, along the second annulus in a first direction, through a heating coil in a second direction opposite the first direction, and through the inner tube. A removable mouthpiece assembly is disposed at an end of the inner tube. A porous ceramic ring has the heating coil disposed on an inner surface and an outer surface in fluid communication with the e-liquid chamber.

BRIEF DESCRIPTION OF THE DRAWINGS

FIG. 3 is a top plan view of the first embodiment of the dual chamber vaporization tank.

FIG. 4 is a cross-sectional view of the first embodiment of the dual chamber vaporization tank taken along the line 4-4 in FIG. 3.

FIG. 5 is a partial cross-sectional view of the first embodiment of the dual chamber vaporization tank taken along the line 4-4 in FIG. 3 illustrating a top airflow aperture in a closed state.

FIG. 6 is a partial cross-sectional view of the first embodiment of the dual chamber vaporization tank taken along the line 4-4 in FIG. 3 illustrating the top airflow aperture in an open state.

Other aspects and advantages of the present invention will become apparent upon consideration of the following detailed description, wherein similar structures have similar reference numerals.

DETAILED DESCRIPTION

The following detailed embodiments presented herein are for illustrative purposes. That is, these detailed embodiments are intended to be exemplary of the present invention for the purposes of providing and aiding a person skilled in the pertinent art to readily understand how to make and use of the present invention.

Figures 1, 2:
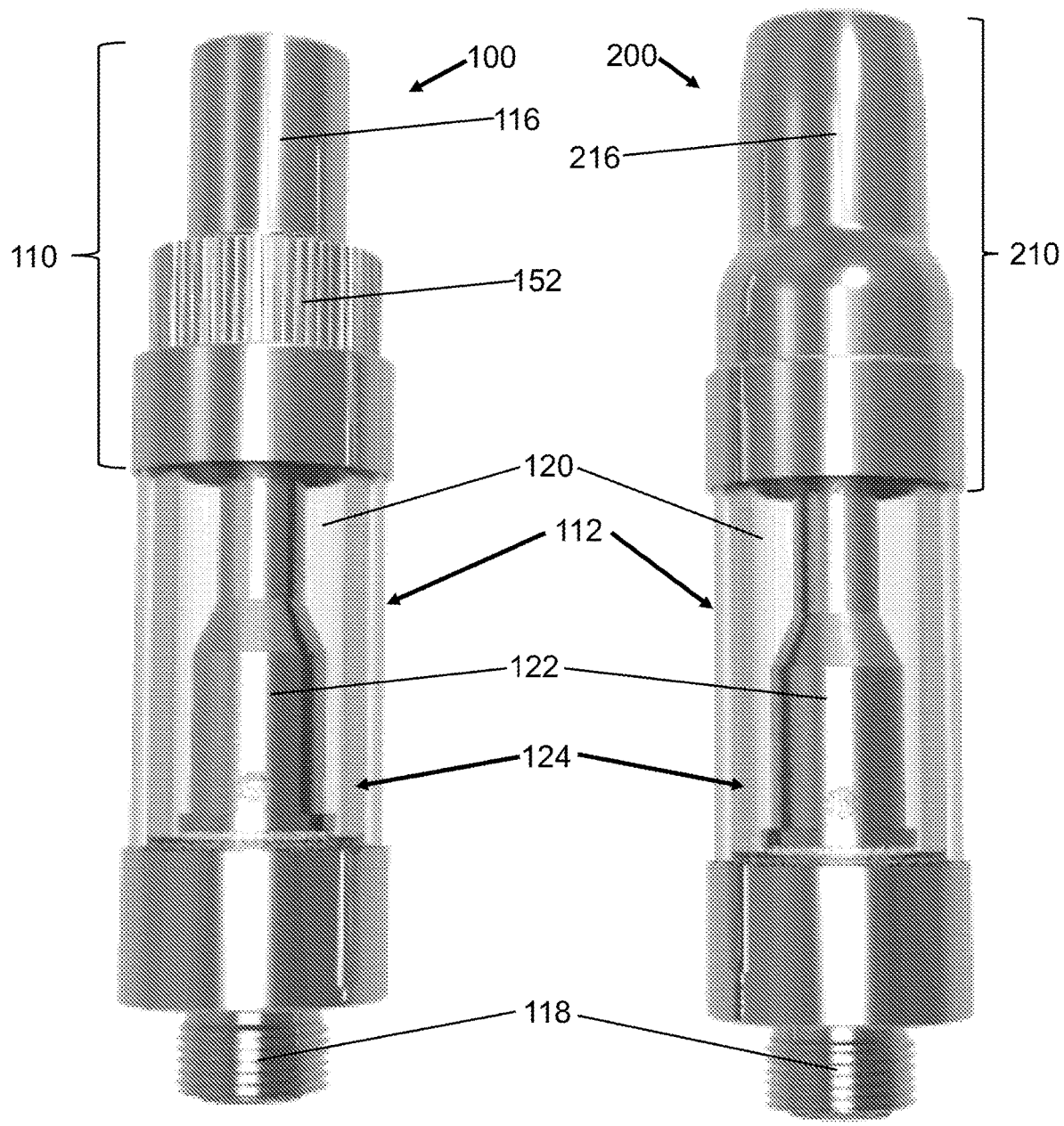
FIG. 1 is a side elevation of a first embodiment of a dual chamber vaporization tank.
FIG. 2 is a side elevation of a second embodiment of the dual chamber vaporization tank.

An embodiment of a dual chamber tank 100 of the present invention is shown in FIG. 1. FIG. 2 shows a second embodiment of a dual chamber tank 200. Both embodiments 100, 200 have an outer tube 112 that is illustrated in FIGS. 1 and 2 to be transparent, though transparency is not required. An inner air tube 122 that also defines an interior surface of an e-liquid chamber 120 is made visible through the transparent outer tube 112 in FIGS. 1 and 2. Both embodiments 100, 200 include threads 118 on a bottom end where a battery (not shown) may engaged to provide power to a heating coil (see cross-sectional views in FIGS. 4, 7, 8, 10, 13, and 14).

The embodiments 100 and 200 are similar in structure except for a mouthpiece assembly 110, 210, disposed respectively, thereon. Mouthpiece assembly 110 disposed at a top end of the first embodiment 100 includes a mouthpiece 116 and a limiting ring 152. As will be described more fully below, rotation of the limiting ring 152 controls the size of a top airflow aperture 150 shown in FIGS. 5 and 6. Mouthpiece assembly 210 on the second embodiment 200 does not include a limiting ring 152, but instead in this embodiment, rotation of the mouthpiece 216 itself controls the size of a top airflow aperture 250 shown in FIGS. 11 and 12.

FIG. 3 shows a top plan view (or mouthpiece end view) looking into a first embodiment of the device 100. FIG. 3 provides a basis for the cross-sectional view of the dual chamber tank 100 shown in FIG. 4.

Referring to FIG. 4, a cross-sectional view of the dual chamber tank 100 shows an interior structure of the tank 100. The outer tube 112 is shown containing and encompassing an inner air tube 122 disposed along the center of the dual chamber tank 100 between a heating coil 142 and the mouthpiece 116. An intermediate tube 124 is disposed between the outer and inner tubes, 112, 122 respectively. The intermediate tube 124 may be made of glass but may also be made from any other suitable materials, for example, metals, ceramics or the like. The mouthpiece assembly 110 comprises the mouthpiece 116, the limiting ring 152, a top cover support 126, a sealing ring 130, and a silicone dampening ring 132.

A bottom of the dual chamber tank 100 comprises the threads 118 housing an anode 134 that operatively connects to a cathode on a battery (not shown). The anode 134 is housed within an insulator 136. Disposed just above the anode 134 is a ceramic support 138 that supports a porous ceramic ring 140. A wick 144 is disposed in contact with an outer surface of the porous ceramic ring 140. E-liquid is absorbed from the e-liquid chamber 120 and supplied to the outer surface of the porous ceramic ring 140 by the wick 144. The e-liquid passes through the porous ceramic ring 140 to the heating coil 142 disposed on an inner surface of the porous ceramic ring 140.

Referring to FIG. 5, in this embodiment the limiting ring 152 is shown in a first position where there is a gap 148 (indicated by the parallel lines) between a bottom shoulder 147 of the mouthpiece 116 and a top of the limiting ring 152, and a bottom of the limiting ring 152 is in contact with a top of the top cover support 126. In this position the top airflow aperture 150 is closed.

Referring to FIG. 6, the limiting ring 152 of this embodiment is shown in a second position reachable from the first position shown in FIG. 5 by a rotation of the limiting ring 152 around the mouthpiece assembly 110. In the second position the top of the limiting ring 152 is in contact with the bottom shoulder 147 of the mouthpiece 116, and there is a gap between the bottom of the limiting ring 152 and the top of the top cover support 126. In this position the top airflow aperture 150 is open (as indicated by the parallel lines).

The limiting ring 152 in this embodiment is internally threaded so that rotation of the limiting ring 152 around the mouthpiece assembly 110 causes a translation of the limiting ring 152 toward or away from the mouthpiece 116. In other embodiments, the translation of the limiting ring 152 toward or away from the mouthpiece 116, and the resulting control of airflow through the top airflow aperture 150 can be facilitated by any means understood by persons skilled in the art, e.g., a threaded connection, a sliding connection, a snap-fit connection, or the like.

Traditional e-liquid tanks having air intake holes at the bottom of the tanks are generally provided with a small delivery aperture, which makes it difficult to accurately fill the tank for filling prescriptions and medicaments, but also makes a mess which could in turn ruin the electronics if exposed to oils in the e-liquids. Imprecise filling of the tanks can result in loss of vaporizable e-liquid, and potentially loss of the electronics of the device, which can be costly. These problems are solved by providing a configuration that has a mouthpiece assembly 110, 210 which can be disengaged thereby exposing the tank for filling. Top airflow apertures 150 that draw air from the top into a path that travels down an annulus and back up through the heating coil helps to draw the vaporized product essentially completely to the user, giving the benefit of airflow from the bottom, while at the same time, protecting the internal electronics from leaks that are typical with bottom airflow apertures.

Figures 7, 8:
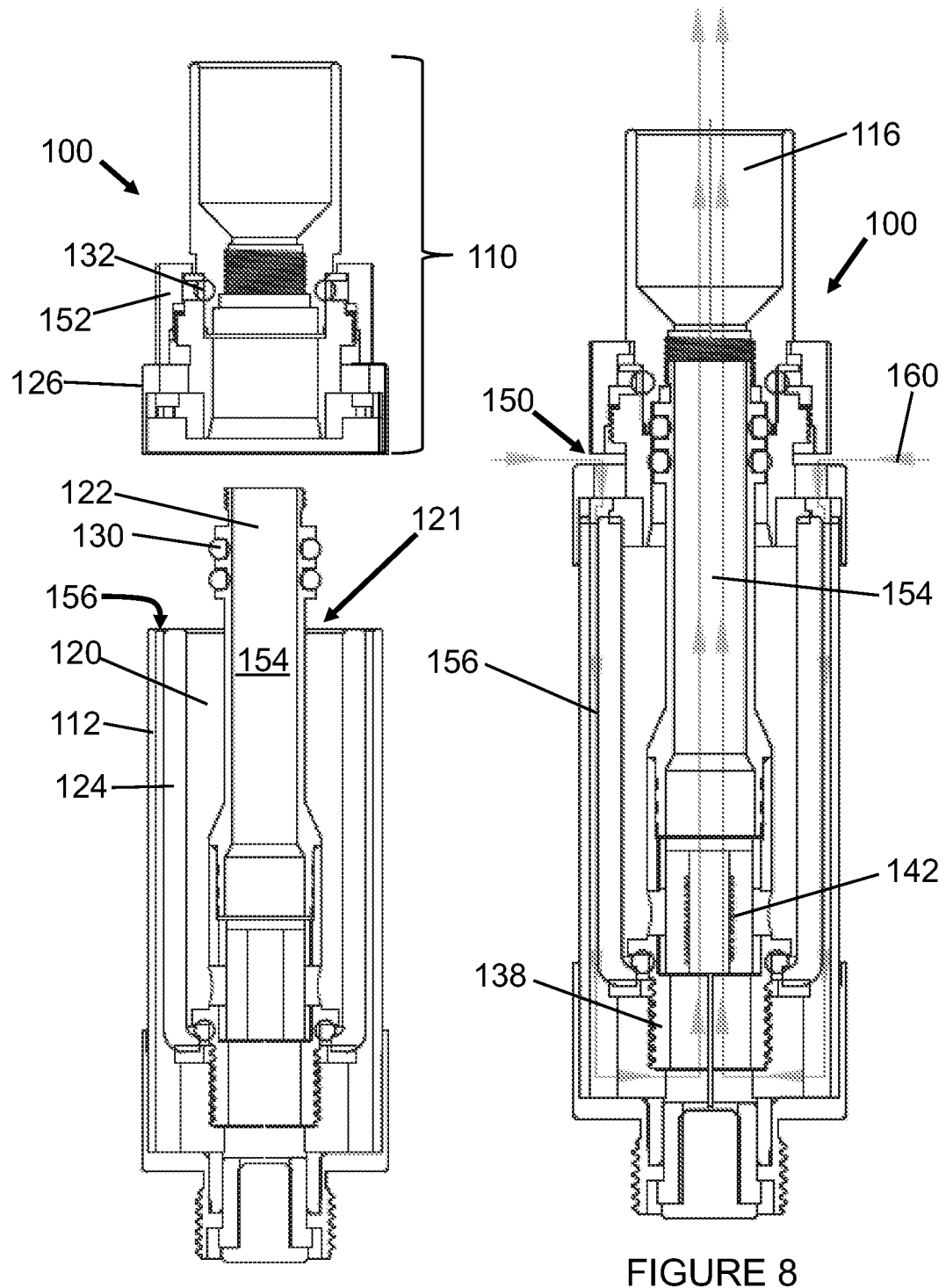
FIG. 7 is a cross-sectional view of the first embodiment of the dual chamber vaporization tank taken along the line 4-4 in FIG. 3 illustrating the mouthpiece assembly separated from the tank assembly.
FIG. 8 is a cross-sectional view of the first embodiment of the dual chamber vaporization tank taken along the line 4-4 in FIG. 3 illustrating airflow paths through the device.

Referring to FIG. 7, the mouthpiece assembly 110 of the dual chamber tank 100 is shown removed from the e-liquid chamber 120. Removal of the mouthpiece assembly 110 as shown exposes an open end 121 of the e-liquid chamber 120 and allows the e-liquid chamber 120 to be filled with e-liquid. The e-liquid chamber 120 is defined by the inner air tube 122 and the intermediate tube 124. The inner air tube 122 isolates an air flow chamber 154 contained therein from the e-liquid chamber 120. Also shown in FIG. 7 is an annular airflow space 156 defined between the outer tube 112 and the intermediate tube 124.

The mouthpiece assembly 110, 210 can attach to the e-liquid chamber 120 by a press-fit over the sealing rings 130, or may attach via threads or via any other suitable method of attachment as may be known in the art. In an embodiment where the mouthpiece assembly 110, 210 attaches to the e-liquid chamber by threads, the threaded attachment may or may not be the same threaded mechanism that controls the size of the airflow aperture as described below with regard to FIGS. 11 and 12.

Referring to FIG. 8, when the mouthpiece assembly 110 is attached to the e-liquid chamber 120 and the top airflow aperture 150 is in an open state, the annular airflow space 156 is in fluid communication with the top airflow aperture 150. As indicated by the arrows 160 in FIG. 8 (several reference numerals have been left off this figure for clarity) a path for ambient air through the device 100 starts at the airflow top aperture 150, travels away from the mouthpiece 116 in the annular airflow space 156, travels under and back up through the ceramic support 138 and then up through the heating coil 142 into the air flow chamber 154 which leads to the mouthpiece 116 (and to a user's mouth).

The ambient airflow path 160 also provides for cooling of the heating coil 142 to help prevent overheating of the e-liquid and the resultant change in properties thereof, which ensures a consistent vapor production on every puff. Cooling the heating coil 142 also allows the heating coil 142 to maintain a more precise temperature for vaporizing the e-liquid and components therein to more readily prevent carcinogens from being inhaled due to imprecise vaporization temperatures, and instead, to retain the intended characteristics of vaporized e-liquid and components therein.

Figure 9:
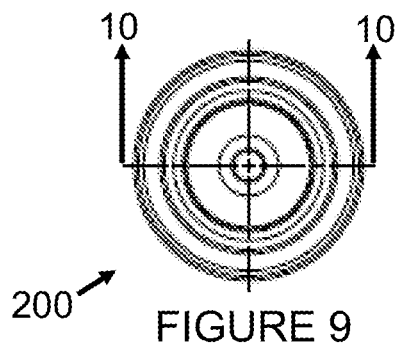
FIG. 9 is a top plan view of the second embodiment of the dual chamber vaporization tank.

FIG. 9 shows a top plan view (or mouthpiece end view) looking into a second embodiment of the device 200. FIG. 9 provides a basis for the cross-sectional view of the dual chamber tank 200 shown in FIG. 10.

Figure 10:
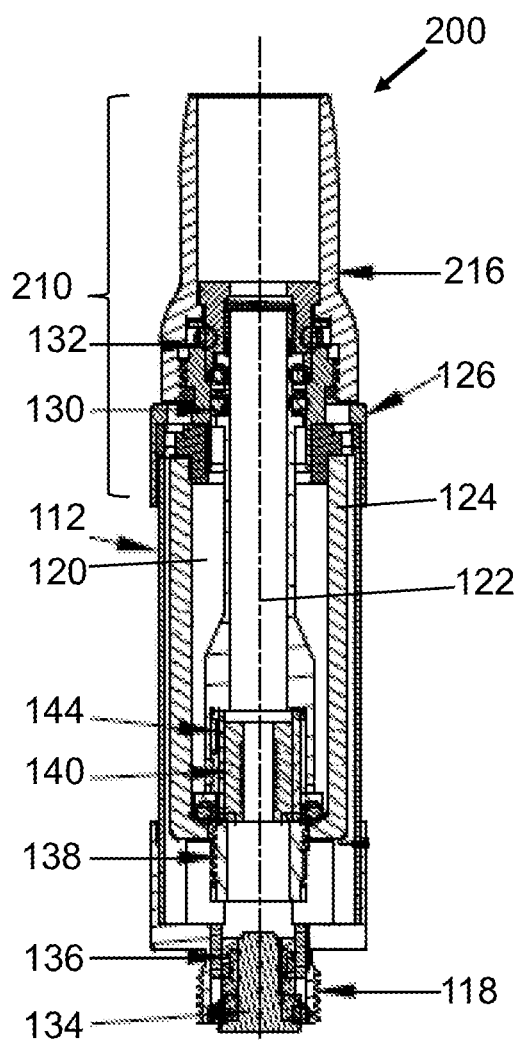
FIG. 10 is a cross-sectional view of the second embodiment of the dual chamber vaporization tank taken along the line 10-10 in FIG. 9.

Referring to FIG. 10, a cross-sectional view of the dual chamber tank 200 shows an interior structure of the tank 200. Most of the internal components in this embodiment are identical to those in the embodiment of the dual chamber tank 100 described above with reference to FIGS. 3-8. The outer tube 112 is shown containing and encompassing the inner air tube 122 disposed along the center of the dual chamber tank 200 between a heating coil 142 and the mouthpiece 216. An intermediate tube 124 is disposed between the outer and inner tubes, 112, 122 respectively. The mouthpiece assembly 210 comprises the mouthpiece 216, the top cover support 126, the sealing ring 130, and the silicone dampening ring 132.

A bottom of the dual chamber tank 200 comprises the threads 118 housing an anode 134 that operatively connects to a cathode on a battery (not shown). The anode 134 is housed within an insulator 136. Disposed just above the anode 134 is a ceramic support 138 that supports a porous ceramic ring 140. A wick 144 is disposed in contact with an outer surface of the porous ceramic ring 140. E-liquid is absorbed from the e-liquid chamber 120 and supplied to the outer surface of the porous ceramic ring 140 by the wick 144. The e-liquid passes through the porous ceramic ring 140 to the heating coil 142 disposed on an inner surface of the porous ceramic ring 140.

Figure 11:
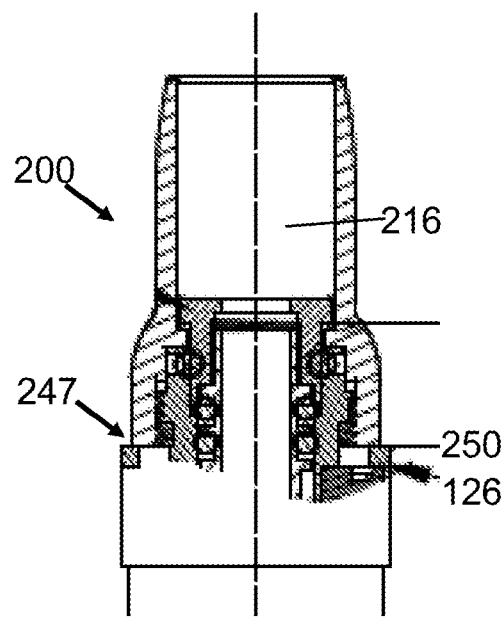
FIG. 11 is a partial cross-sectional view of the second embodiment of the dual chamber vaporization tank taken along the line 10-10 in FIG. 9 illustrating a top airflow aperture in a closed state.

Referring to FIG. 11, in this embodiment the mouthpiece 216 is shown in a first position where a bottom edge 247 of the mouthpiece 216 is in contact with a top of the top cover support 126. In this position the top airflow aperture 250 is closed.

Figure 12:
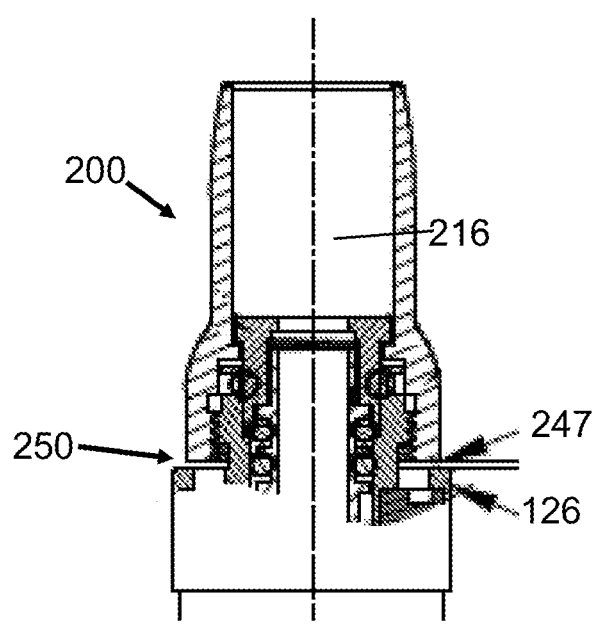
FIG. 12 is a partial cross-sectional view of the second embodiment of the dual chamber vaporization tank taken along the line 10-10 in FIG. 9 illustrating a top airflow aperture in an open state.

Referring to FIG. 12, the mouthpiece 216 of this embodiment is shown in a second position reachable from the first position shown in FIG. 11 by a rotation of the mouthpiece 216 around the mouthpiece assembly 210. In the second position there is a gap (as indicated by the parallel lines) between the bottom edge 247 of the mouthpiece 216 and the top of the top cover support 126. In this position the top airflow aperture 250 is open.

The mouthpiece 216 in this embodiment is internally threaded so that rotation of the mouthpiece 216 around the mouthpiece assembly 210 causes a translation of the mouthpiece 216 toward or away from the top cover support 126. In other embodiments, the translation of the mouthpiece 216 toward or away from the top cover support 126, and the resulting control of airflow through the top airflow aperture 250 can be facilitated by any means understood by persons skilled in the art, e.g., a threaded connection, a sliding connection, a snap-fit connection, or the like.

Figures 13, 14:
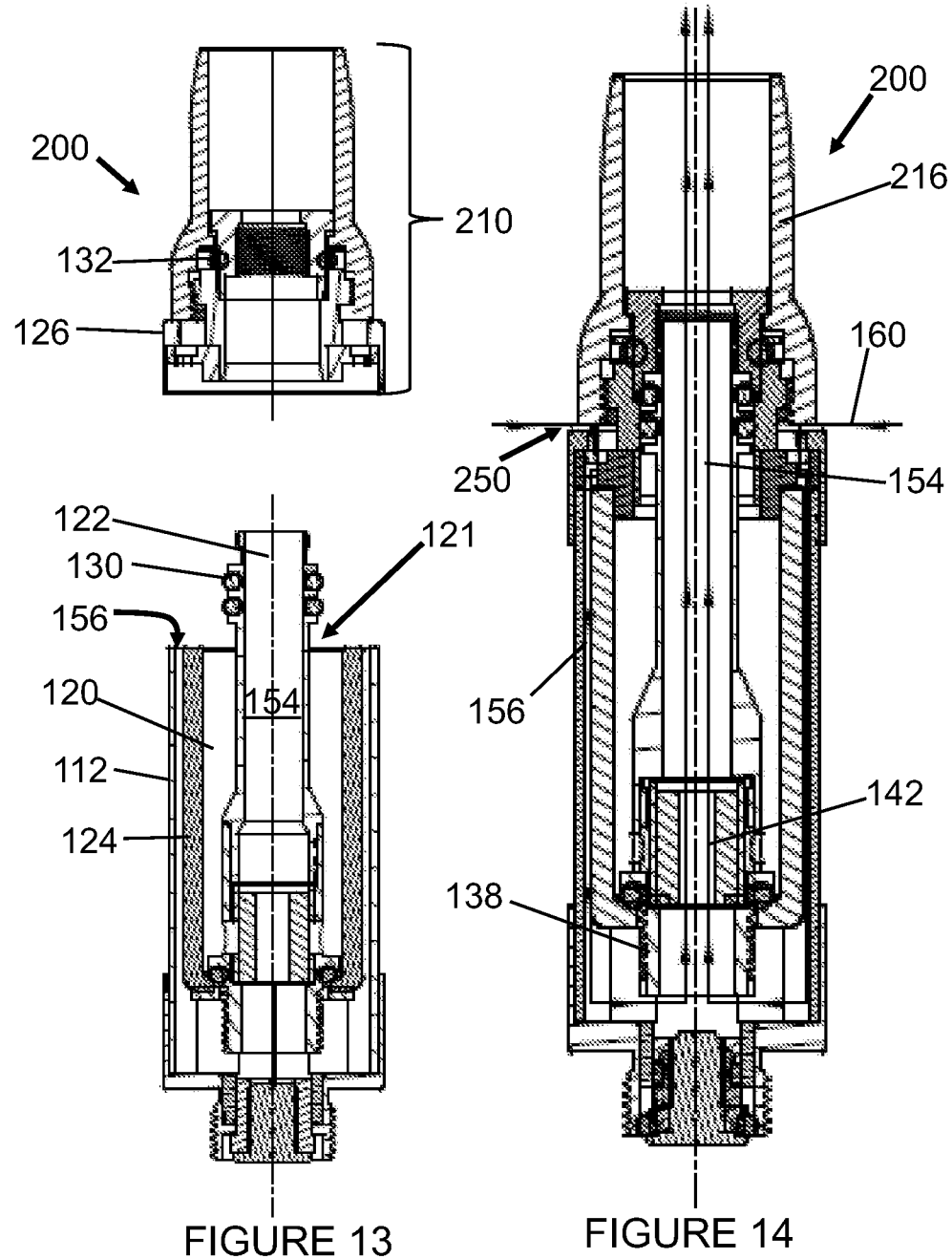
FIG. 13 is a cross-sectional view of the second embodiment of the dual chamber vaporization tank taken along the line 10-10 in FIG. 9 illustrating the mouthpiece assembly separated from the tank assembly.
FIG. 14 is a cross-sectional view of the second embodiment of the dual chamber vaporization tank taken along the line 10-10 in FIG. 9 illustrating airflow paths through the device.

Referring to FIG. 13, the mouthpiece assembly 210 of the dual chamber tank 200 is shown removed from the e-liquid chamber 120. Removal of the mouthpiece assembly 210 as shown exposes an open end 121 of the e-liquid chamber 120 and allows the e-liquid chamber 120 to be filled with e-liquid. The e-liquid chamber 120 is defined by the inner air tube 122 and the intermediate tube 124. The inner air tube 122 isolates an air flow chamber 154 contained therein from the e-liquid chamber 120. Also shown in FIG. 13 is the annular airflow space 156 defined between the outer tube 112 and the intermediate tube 124.

Referring to FIG. 14, when the mouthpiece assembly 210 is attached to the e-liquid chamber 120 and the top airflow aperture 250 is in an open state, the annular airflow space 156 is in fluid communication with the top airflow aperture 250. As indicated by the arrows 160 in FIG. 14 (several reference numerals have been left off this figure for clarity) a path for ambient air through the device 200 starts at the airflow top aperture 250, travels away from the mouthpiece 216 in the annular airflow space 156, travels under and back up through the ceramic support 138 and then up through the heating coil 142 into the air flow chamber 154 which leads to the mouthpiece 216 (and to a user's mouth).

In some embodiments of the invention, a dual coil can be accommodated in the tank, and in some embodiments, a wick can be ceramic with an embedded coil. Some embodiments also have medical grade materials for the components providing for a more desirable material and tank for the use in medical applications. The embedded coil provides more surface area of the vapor wick and coil combination for more vapor production.

It is to be understood that the mouthpiece 116, 216 can be of any shape desired and/or which is ergonomically suitable. It is also to be understood that the mouthpiece 116, 216 can be provided in a color-coded scheme, identifying different mouthpieces with different purposes and users in mind.

The operation of a vaping device utilizing the dual chamber tank 100, 200 proceeds as follows. Upon filling of the e-liquid chamber 120 with a desired e-liquid and applying the mouthpiece assembly 110, 210 to the e-liquid chamber, the assembled device 100, 200 is attached to a battery via the threads 118 or by other means of attachment as may be known in the art. Electrical connections between the battery and the anode 134 and a cathode that may be an outer housing or another lead not shown completes a circuit with the heating coil to apply power from the battery to the heating coil. The battery circuit typically has a switch that is actuated by a sensor or a user action, for example, there may be a sensor disposed on the device 100, 200 that detects a drop in air pressure that might be caused by a user inhaling on the mouthpiece 116, 216. Upon sensing the drop in pressure, the sensor would signal a control circuit or microprocessor or the like to complete the battery circuit with the heating coil 142. Thus, energizing the heating coil 142 is responsive to a user puffing on the device. E-liquid captured via the wick 144 and supplied to the heating coil 142 through the porous ceramic 140 gets vaporized when the heating coil 142 gets energized. The airflow path 160 as described above brings in ambient air to entrain the vaporized e-liquid substantially in its entirety for delivery up the inner tube 122 to the mouthpiece 116, 216. Other variations on the function of a vaping device are known to one of ordinary skill in the art.

Those skilled in the art will appreciate that the invention described herein is susceptible to variations and modifications other than those specifically described, and that each embodiment is also provided with features that may be applicable to other embodiments. It is to be understood that the invention includes all such variations and modifications that fall within its spirit and scope. The invention also includes all the steps, features, compositions and compounds referred to or indicated in this specification, individually or collectively, and any and all combinations of any two or more of said steps or features.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

INDUSTRIAL APPLICABILITY

The dual chamber vaporization tank includes an annular e-liquid chamber and a top airflow aperture. A mouthpiece assembly controls the size of the top airflow aperture, which when open directs ambient air into an annulus between the e-liquid chamber and an outer tube. Ambient air entering the device flows along the annulus away from the mouthpiece before turning back through a heating coil and flowing up a central tube to a mouthpiece. Flow of ambient air through the coil helps to cool the coil to prevent overheating of the e-liquid and disposing the airflow aperture at a top of the device helps to prevent leaks of e-liquid from the device. The dual chamber vaporization device can be manufactured and used in industry.

Numerous modifications to the present invention will be apparent to those skilled in the art in view of the foregoing description. It is not desired to limit the invention to the exact construction and operation shown and described, and accordingly, all suitable modifications and equivalents may be resorted to, falling within the scope of the invention. Accordingly, this description is to be construed as illustrative only of the principles of the invention and is presented for the purpose of enabling those skilled in the art to make and use the invention and to teach the best mode of carrying out same. The exclusive rights to all modifications which come within the scope of the appended claims are reserved. All patents, patent publications and applications, and other references cited herein are incorporated by reference herein in their entirety.

I claim:

1. A dual chamber vaporization tank, comprising:
an inner tube assembly, an intermediate tube, and an outer tube;
the inner tube assembly comprising an inner tube and a porous ceramic ring disposed at an end of the inner tube, the porous ceramic ring having a heating coil disposed on an inner surface thereof;
an e-liquid chamber defined by a first annulus between the inner tube assembly and the intermediate tube; and
a second annulus between the intermediate tube and the outer tube, wherein the second annulus is free from airflow resisting obstruction;
wherein an airflow path is defined through the second annulus in a first direction and through the inner tube assembly in a second direction opposite the first direction.

2. The dual chamber vaporization tank of claim 1, wherein a mouthpiece assembly removably attaches over the inner tube and has a passage that provides fluid communication between the air flow path and ambient air.

3. The dual chamber vaporization tank of claim 2, wherein an opening of the passage can be closed and adjusted in size.

4. The dual chamber vaporization tank of claim 3, wherein the mouthpiece assembly includes a limiting ring that continuously moves between a first position where the opening is closed and a plurality of second positions where the opening is open and has a plurality of sizes.

5. The dual chamber vaporization tank of claim 3, wherein the mouthpiece assembly comprises a mouthpiece that continuously moves between a first position where the opening is closed and a plurality of second positions where the opening is open and has a plurality of size.

6. The dual chamber vaporization tank of claim 4, wherein the limiting ring continuously moves between the first position and the plurality of second positions by rotating on threads.

7. The dual chamber vaporization tank of claim 2, wherein e-liquid passes through the porous ceramic ring and is vaporized by the heating coil, and the ambient air flows along the airflow path through the heating coil to entrain substantially all the vaporized e-liquid.

8. The dual chamber vaporization tank of claim 7, wherein the ambient air that flows along the airflow path through the heating coil cools the heating coil.

9. The dual chamber vaporization tank of claim 2, wherein removing the mouthpiece assembly exposes an open end of the e-liquid chamber.

10. A dual chamber vaporization tank, comprising:
an inner tube assembly comprising an inner tube and a porous ceramic ring disposed at a first end of the inner tube, the porous ceramic ring having a heating coil disposed on an inner surface thereof;
an e-liquid chamber defined by a first annulus between the inner tube assembly and an intermediate tube;
a second annulus between the intermediate tube and an outer tube, wherein the second annulus is free from airflow resisting obstruction; and
an airflow path defined through the second annulus in a first direction and through the inner tube assembly in a second direction opposite the first direction; and
a removable mouthpiece assembly disposed at a second end of the inner tube.

11. The dual chamber vaporization tank of claim 10, wherein removing the removable mouthpiece exposes an open end of the e-liquid chamber.

12. The dual chamber vaporization tank of claim 10 further comprising a wick disposed on an outer surface of the porous ceramic ring.

13. The dual chamber vaporization tank of claim 11, wherein the removable mouthpiece assembly has a passage that provides fluid communication between the air flow path and ambient air, wherein an opening of the passage can be closed and adjusted in size.

14. The dual chamber vaporization tank of claim 13, wherein the removable mouthpiece assembly includes a mechanism that moves continuously between a first position where the opening is closed and a plurality of second positions where the opening is open and has a plurality of sizes.

15. The dual chamber vaporization tank of claim 14, wherein the mechanism moves between the first position and the plurality of second positions by rotating on threads.

16. The dual chamber vaporization tank of claim 15, wherein the mechanism comprises a mouthpiece.

17. The dual chamber vaporization tank of claim 15, wherein the mechanism comprises a limiting ring.

18. The dual chamber vaporization tank of claim 10, wherein e-liquid passes through the porous ceramic ring and is vaporized by the heating coil, and the ambient air flows along the airflow path through the heating coil to entrain substantially all the vaporized e-liquid.

19. The dual chamber vaporization tank of claim 18, wherein the ambient air that flows along the airflow path through the heating coil cools the heating coil.

20. The dual chamber vaporization tank of claim 5, wherein the mouthpiece continuously moves between the first position and the plurality of second positions by rotating on threads.

* * * * *